United States Patent
Nanjo (10) Patent No.: US 12,094,593 B2
(45) Date of Patent: Sep. 17, 2024

(54) MEDICAL IMAGE DISPLAY SYSTEM, MEDICAL IMAGE DISPLAY TERMINAL, AND RECORDING MEDIUM

(71) Applicant: Konica Minolta, Inc., Tokyo (JP)

(72) Inventor: Takafumi Nanjo, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 18/198,446

(22) Filed: May 17, 2023

(65) Prior Publication Data
US 2023/0377722 A1 Nov. 23, 2023

(30) Foreign Application Priority Data
May 20, 2022 (JP) ................................ 2022-082669

(51) Int. Cl.
| | |
|---|---|
| G06T 1/00 | (2006.01) |
| G06T 11/00 | (2006.01) |
| G16H 30/20 | (2018.01) |

(52) U.S. Cl.
CPC ............. *G16H 30/20* (2018.01); *G06T 11/00* (2013.01); *G06T 2210/32* (2013.01); *G06T 2210/41* (2013.01)

(58) Field of Classification Search
CPC ........ G16H 30/20; G16H 30/40; G06T 11/00; G06T 2210/32; G06T 2210/41
See application file for complete search history.

(56) References Cited

U.S. PATENT DOCUMENTS

| | | | | |
|---|---|---|---|---|
| 8,625,135 | B2* | 1/2014 | Towata | H04N 1/0023 |
| | | | | 709/201 |
| 8,654,139 | B2* | 2/2014 | Jakobovits | G16H 30/40 |
| | | | | 345/589 |
| 9,229,931 | B2* | 1/2016 | Klotzer | G06F 3/04812 |
| 9,569,841 | B2* | 2/2017 | Fujii | A61B 8/5269 |
| 2002/0016718 | A1* | 2/2002 | Rothschild | G16H 30/20 |
| | | | | 705/2 |

(Continued)

FOREIGN PATENT DOCUMENTS

| | | | | |
|---|---|---|---|---|
| CN | 103838813 B | * | 3/2019 | ......... G06F 16/9577 |
| CN | 106170799 B | * | 1/2021 | ........... G06F 17/241 |

(Continued)

OTHER PUBLICATIONS

CN103838813B English translation, publication date: Mar. 22, 2019, pp. 1-21 (Year: 2019).*

*Primary Examiner* — Laurie A Ries
(74) *Attorney, Agent, or Firm* — Osha Bergman Watanabe & Burton LLP (57) ABSTRACT

A medical image display system includes a server, and a medical image display terminal that communicates with the server. The server includes a storage that stores medical image data in a storage format, and a first transmitter that transmits the medical image data in the storage format to the medical image display terminal. The medical image display terminal includes a first hardware processor that converts the medical image data in the storage format transmitted from the server into medical image data in a viewing format that is viewable on a web browser, and a display that displays a medical image based on the medical image data in the viewing format on the web browser.

8 Claims, 6 Drawing Sheets

(56) References Cited

U.S. PATENT DOCUMENTS

| | | | | |
|---|---|---|---|---|
| 2002/0133373 A1* | 9/2002 | Silva-Craig | ............ | G16H 30/40 705/2 |
| 2006/0056680 A1* | 3/2006 | Stutsman | ................ | G06T 15/08 382/154 |
| 2008/0021834 A1* | 1/2008 | Holla | ..................... | G16H 80/00 705/51 |
| 2009/0059772 A1* | 3/2009 | Samari | .................. | G16H 10/20 |
| 2010/0011087 A1* | 1/2010 | Hofsetter | ............... | G06Q 20/40 709/217 |
| 2011/0222117 A1* | 9/2011 | Inose | .................... | G06F 3/1204 358/1.15 |
| 2013/0332179 A1* | 12/2013 | Girard | .................... | G16H 40/67 705/2 |
| 2014/0143299 A1* | 5/2014 | Klotzer | ..................... | G06F 9/54 709/203 |
| 2015/0237106 A1* | 8/2015 | Golay | .................... | A61B 6/563 348/66 |
| 2016/0055618 A1* | 2/2016 | Karpenko | ............. | G06F 3/1454 345/619 |
| 2017/0005994 A9* | 1/2017 | Westin | .................. | G06F 21/602 |
| 2018/0046760 A1* | 2/2018 | Suzuki | .................. | G16H 30/20 |
| 2018/0068131 A1* | 3/2018 | Bronkalla | ........... | G06F 21/6245 |
| 2018/0292963 A1* | 10/2018 | Nanjo | ................. | G06F 3/04855 |
| 2019/0278869 A1* | 9/2019 | Wilson | .................. | G06F 16/986 |
| 2019/0304590 A1* | 10/2019 | Wilson | .................. | G16H 30/20 |
| 2021/0383905 A1* | 12/2021 | Kikuchi | ................ | G16H 30/40 |

FOREIGN PATENT DOCUMENTS

| | | | | |
|---|---|---|---|---|
| JP | 2003324737 A | 11/2003 | | |
| JP | 2014102835 A | 6/2014 | | |
| WO | WO-2013182904 A1 * | 12/2013 | .......... | G06F 19/321 |
| WO | WO-2014050606 A1 * | 4/2014 | .......... | G06F 19/321 |

* cited by examiner

MEDICAL IMAGE DISPLAY SYSTEM, MEDICAL IMAGE DISPLAY TERMINAL, AND RECORDING MEDIUM

CROSS-REFERENCE TO RELATED APPLICATIONS

The entire disclosure of Japanese Patent Application No. 2022-082669 filed on May 20, 2022, including description, claims, drawings, and abstract, is incorporated herein by reference.

BACKGROUND

Technical Field

The present invention relates to a medical image display system, a medical image display terminal, and a recording medium storing instructions.

Description of Related Art

Conventionally, there has been known a medical image display system that enables medical images stored in a server to be viewed on a medical image display terminal. Medical images are usually stored in a server in a storage format, such as a DICOM standard. However, medical images in the storage format are not recognized as image files by a web browser installed on a medical image display terminal. For this reason, in order to view a medical image on the medical image display terminal, it is necessary to convert the medical image in the storage format into a medical image in another format (viewing format) that can be viewed on the web browser of the medical image display terminal.

Therefore, there is known an invention in which a medical image converted to a viewing format is stored in advance in a server separately from a medical image in a storage format (see JP 2003-324737 A) or an invention in which a server converts a medical image in a storage format into a medical image in a viewing format in response to an image display request (see JP 2014-102835 A).

However, the invention disclosed in JP 2003-324737 A needs to store both the storage-format medical images and the viewing-format medical images in the server, and accordingly the storage cost increases. In addition, the invention disclosed in JP 2014-102835 A has a tendency that, when a server receives a number of image display requests at the same time, the amount of processing for conversion into the viewing format increases to become a burden.

SUMMARY

One or more embodiments of the present invention deal with such issues, and provide a medical image display system, a medical image display terminal, and a recording medium storing instructions capable of reducing a burden on a server and reducing the cost.

According to one or more embodiments of the present invention, a medical image display system comprises: a server; and a medical image display terminal that communicates with the server. The server includes a storage that stores medical image data in a storage format, and a first transmitter that transmits the medical image data in the storage format to the medical image display terminal. The medical image display terminal includes a first hardware processor that converts the medical image data in the storage format transmitted from the server into medical image data in a viewing format that is viewable on a web browser, and a display that displays a medical image based on the medical image data in the viewing format on the web browser.

According to one or more embodiments of the present invention, a medical image display terminal that communicates with a server, and comprises: a first hardware processor that converts medical image data in a storage format transmitted from the server into medical image data in a viewing format that is viewable on a web browser; and a display that displays a medical image based on the medical image data in the viewing format on the web browser.

According to one or more embodiments of the present invention, a non-transitory computer readable recording medium stores instructions causing a computer of a medical image display terminal that communicates with a server to execute: converting medical image data in a storage format transmitted from the server into medical image data in a viewing format that is viewable on a web browser; and displaying a medical image based on the medical image data in the viewing format on the web browser.

BRIEF DESCRIPTION OF THE DRAWINGS

The advantages and features provided by one or more embodiments of the invention will become more fully understood from the detailed description hereinbelow and the appended drawings which are given by way of illustration only, and thus are not intended as a definition of the limits of the present invention, wherein.

DETAILED DESCRIPTION

Hereinafter, embodiments of the present invention will be described with reference to the drawings. However, the scope of the invention is not limited to the disclosed embodiments.

[Configuration of a Medical Image Display System]

Figure 1:
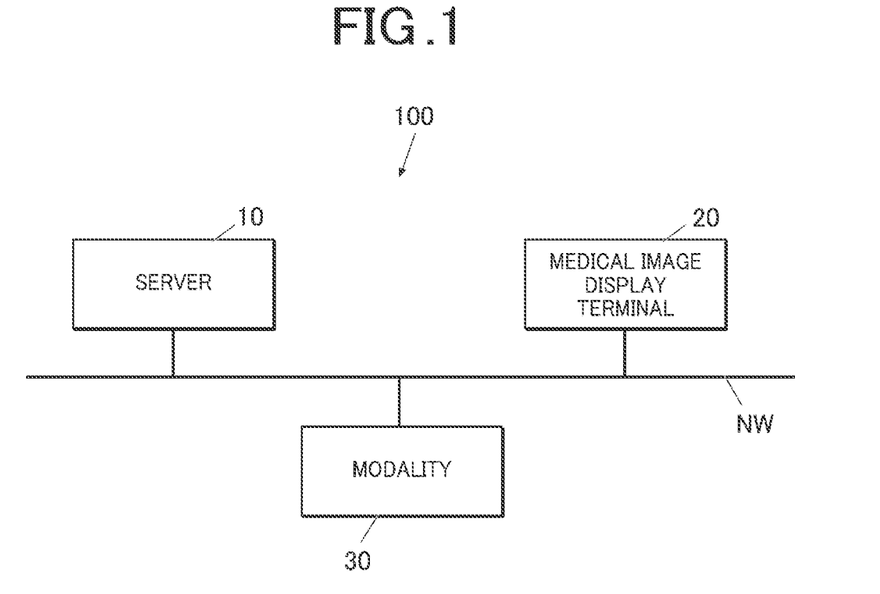
FIG. 1 is a schematic configuration diagram of a medical image display system according to one or more embodiments.

FIG. 1 shows a schematic configuration diagram of a medical image display system 100 according to one or more embodiments.

The medical image display system 100 includes a server 10, a medical image display terminal 20, and a modality 30. The server 10, the medical image display terminal 20, and the modality 30 are connected to each other by a network ("NW"), so that various kinds of data or signals can be transmitted and received therebetween.

In FIG. 1, the medical image display system 100 is shown in an example in which one medical image display terminal 20 and one modality 30 are connected to one server 10. However, the present invention is not limited thereto, any of those components described above may be provided in a plural number. The network NW is preferably a wireless connection, but may be a wired connection.

[Server]

Figure 2:
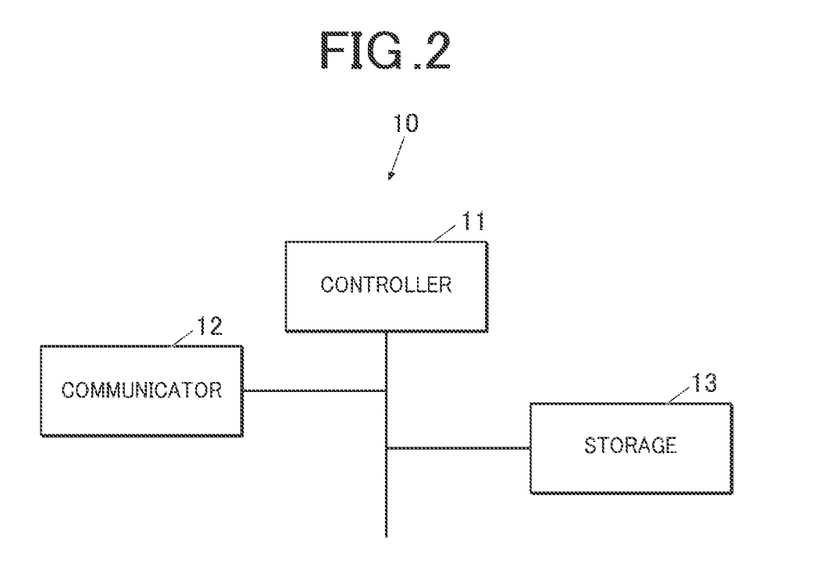
FIG. 2 is a functional block diagram of a server.

FIG. 2 is a block diagram showing an example of the functional configuration of the server 10.

As shown in FIG. 2, the server 10 includes a controller (a second hardware processor in one or more embodiments) 11, a communicator or communication interface (a first transmitter/receiver in one or more embodiments) 12, a storage 13, and the like, and these are connected to each other by a bus.

The server 10 forms a PACS (picture archiving and communication system; medical image management system).

The server 10 is connected to the modality 30 (for example, CR (computed radiography), CT (computed tomography), and/or MRI (magnetic resonance imaging)), and receives medical image data in a storage format obtained by imaging by the modality 30 from the modality 30. Then, the server 10 stores the received medical image data in a storage format in the storage 13 and manages the medical image data for each patient.

In one or more embodiments, the server 10 and the modality 30 conforms to the DICOM (digital image and communications in medicine) standard, and communication between these devices is performed according to the DICOM. In one or more embodiments, the "medical image data in a storage format" refers to data in the DICOM format. Medical image data in the DICOM format includes an image portion and an additional information portion. Actual data as a medical image is written in the image portion, and various kinds of additional information relevant to the medical image are written in the additional information portion.

The "medical image data in a storage format" is not limited to data in the DICOM format.

The server 10 may be provided as a tangible device and operated on-premises, or may be provided in a cloud environment without a tangible device.

When the server 10 is provided as a device, a display or an operation interface may be provided in the device so that a medical image ("P") can be displayed or various kinds of image processing can be performed in the vicinity of the server 10.

(Controller)

The controller 11 includes a CPU (central processing unit), a RAM (random access memory), a ROM (read only memory), and the like. The controller 11 performs overall control of the processing operations of the respective units of the server 10. Specifically, various processing programs (or instructions) stored in the ROM are read out and loaded to the RAM according to various signals (for example, an image or data transmission request signal) from the medical image display terminal 20 that are received by the communicator 12, and the CPU performs various processes in cooperation with the processing programs.

(Communicator)

The communicator 12 is a network interface or the like. The communicator 12 transmits and receives data to and from an external device connected through the network NW, such as a LAN (local area network), a WAN (wide area network), and the Internet.

(Storage)

The storage 13 is an HDD (hard disk drive), an SSD (solid state drive), or the like. The storage 13 stores various processing programs (or instructions), parameters and files necessary for executing the processing programs, and the like.

Specifically, for example, the storage 13 stores a web server program causing a web browser to function as a web server that provides various web contents to the web browser by communicating with a web browser installed on the medical image display terminal 20 using an HTTP protocol. The storage 13 also stores a web application program that operates on the web server and generates a web screen for displaying the medical image P on the medical image display terminal 20 through the web browser. The storage 13 also stores a conversion processing program for converting medical image data in a storage format into medical image data in a viewing format (for example, BMP, JPEG, PNG, or MPEG).

The storage 13 also has a database for managing medical image data transmitted from the modality 30. Predetermined additional information, such as patient name, examination type, and date, is attached to the additional information portion of the medical image data, so that each piece of medical image data can be identified.

The medical image data handled by the medical image display system 100 according to one or more embodiments include single image data (single-frame image) that forms a single image and a plurality of images (multi-frame images) that appear as a series of moving images when displayed consecutively.

(Operation of a Server)

The server 10 configured as described above performs the following operations through software processing in cooperation between the controller 11 and the program stored in the storage 13.

Figure 3:
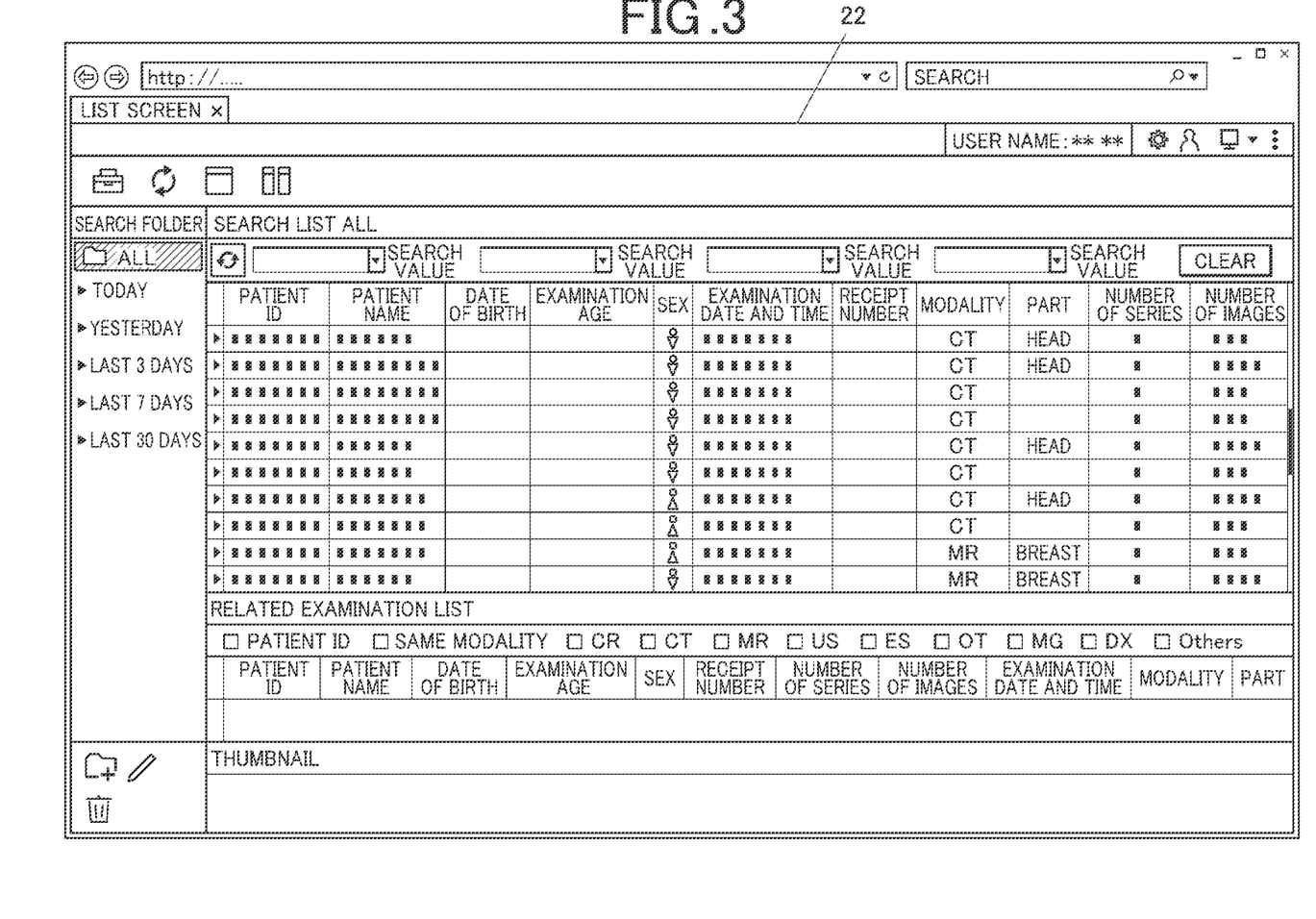
FIG. 3 is a schematic diagram of a list screen showing a list of medical image data.

For example, the controller 11 extracts only necessary information from a database for managing medical image data in the storage 13, and then generates a list screen listing the medical image data as shown in FIG. 3. As shown in FIG. 3, the "necessary information" referred to herein specifically includes predetermined additional information, such as patient name, examination type, and date, but does not include the medical image P itself.

When an image transmission request is received from the medical image display terminal 20, if the target medical image data is a multi-frame image, the controller 11 performs division processing to divide the multi-frame image into frames.

The controller 11 has a function of compressing the medical image data stored in the storage 13 and transmitting the compressed medical image data to the medical image display terminal 20 through the communicator 12 based on an image transmission request received from the medical image display terminal 20.

The data compression format is preferably a lossless compression format, such as ZIP or JPEG2000, in which the original data completely matches data after compression/decompression.

[Medical Image Display Terminal]

Figure 4:
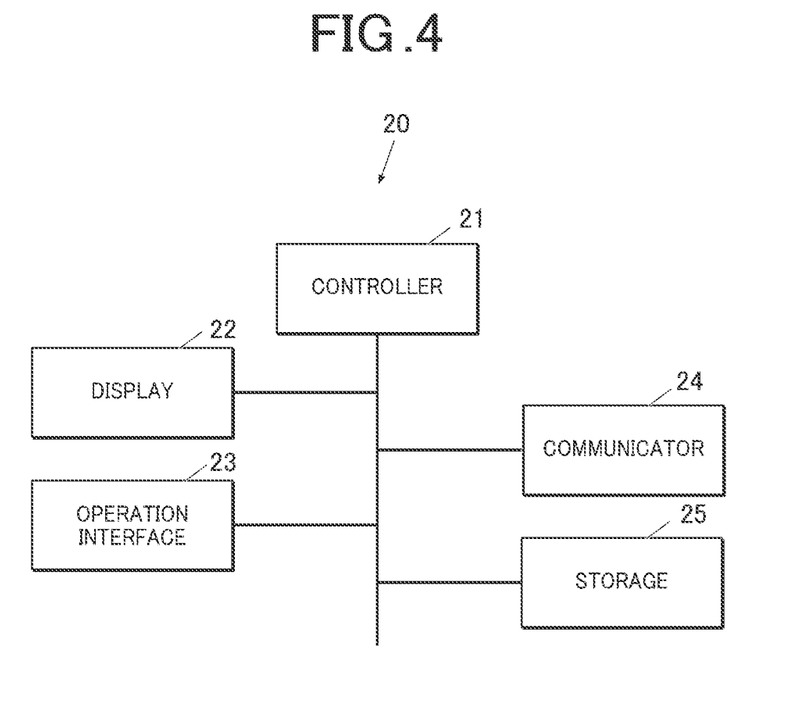
FIG. 4 is a functional block diagram of a medical image display terminal.

FIG. 4 is a block diagram showing an example of the functional configuration of the medical image display terminal 20. As shown in FIG. 4, the medical image display terminal 20 includes a controller (a first hardware processor in one or more embodiments) 21, a display 22, an operation interface 23, a communicator or communication interface (a second transmitter/receiver in one or more embodiments) 24, a storage 25, and the like. These are connected to each other by a bus.

The medical image display terminal 20 is a device for displaying the medical image P, and is used by users such as doctors, nurses, and home-visit care workers in facilities such as hospitals, clinics, home-visit care offices, and homes of patients undergoing home care.

The medical image display terminal 20 may be a PC (personal computer) installed at a predetermined location, or may be a portable mobile terminal such as a tablet or a smart phone.

(Controller)

The controller 21 includes a CPU, a RAM, a ROM, and the like, and performs overall control of the processing operations of the respective units of the medical image display terminal 20. Specifically, various display signals are transmitted to the display 22 by reading out and executing an application program (or instructions) stored in the storage 25 according to an operation signal input through the operation interface 23. A non-transitory computer readable recording medium stores instructions that cause a computer of a medical image display terminal 20 to: convert medical image data in a storage format transmitted from the server 10 into medical image data in a viewing format that is viewable on a web browser; and display a medical image based on the medical image data in the viewing format on the web browser. The medical image display terminal 20 may communicate with the server 10.

(Display)

The display 22 includes a monitor, such as a liquid crystal display (LCD), and displays various screens according to the instruction of a display signal input from the controller 21. The display 22 displays, for example, a list screen of medical image data stored in the server 10 based on display data for various web screens received from the server 10. Medical image data selected on the list screen is displayed as the medical image P.

(Operation Interface)

The operation interface 23 is, for example, a keyboard including various keys, a pointing device such as a mouse, or a touch panel laminated on the display 22. The operation interface 23 outputs to the controller 21 an operation signal input according to the position of a key operation or mouse operation on a keyboard or a touch operation on a touch panel.

(Communicator)

The communicator 24 is a network interface or the like, and transmits and receives data to and from an external device (the server 10 or the modality 30) connected through a communication network "N," such as a LAN, a WAN, or the Internet.

The communicator 24 may perform wireless communication using a mobile phone line or the like to transmit and receive data to and from an external device connected through the communication network N.

(Storage)

The storage 25 is an HDD (hard disk drive), an SSD (solid state drive), or the like. The storage 25 stores programs (or instructions) for the controller 21 to execute various processes, parameters and files necessary for executing the programs, and the like. In particular, the storage 25 stores a web browser program for implementing a web browser.

(Operation of a Medical Image Display Terminal)

The controller 21 of the medical image display terminal 20 configured as described above receives medical image data in a storage format or various processing programs (or instructions) from the server 10 to perform the following operations.

For example, the controller 21 serves as a first conversion processor that converts the medical image data in a storage format into medical image data in a viewing format by rendering using a conversion processing program. In particular, when the medical image data in a storage format received from the server 10 is losslessly compressed image data, the medical image data in the storage format is converted into medical image data in a viewing format after performing decompression processing by the decompression processing program.

Figure 5:
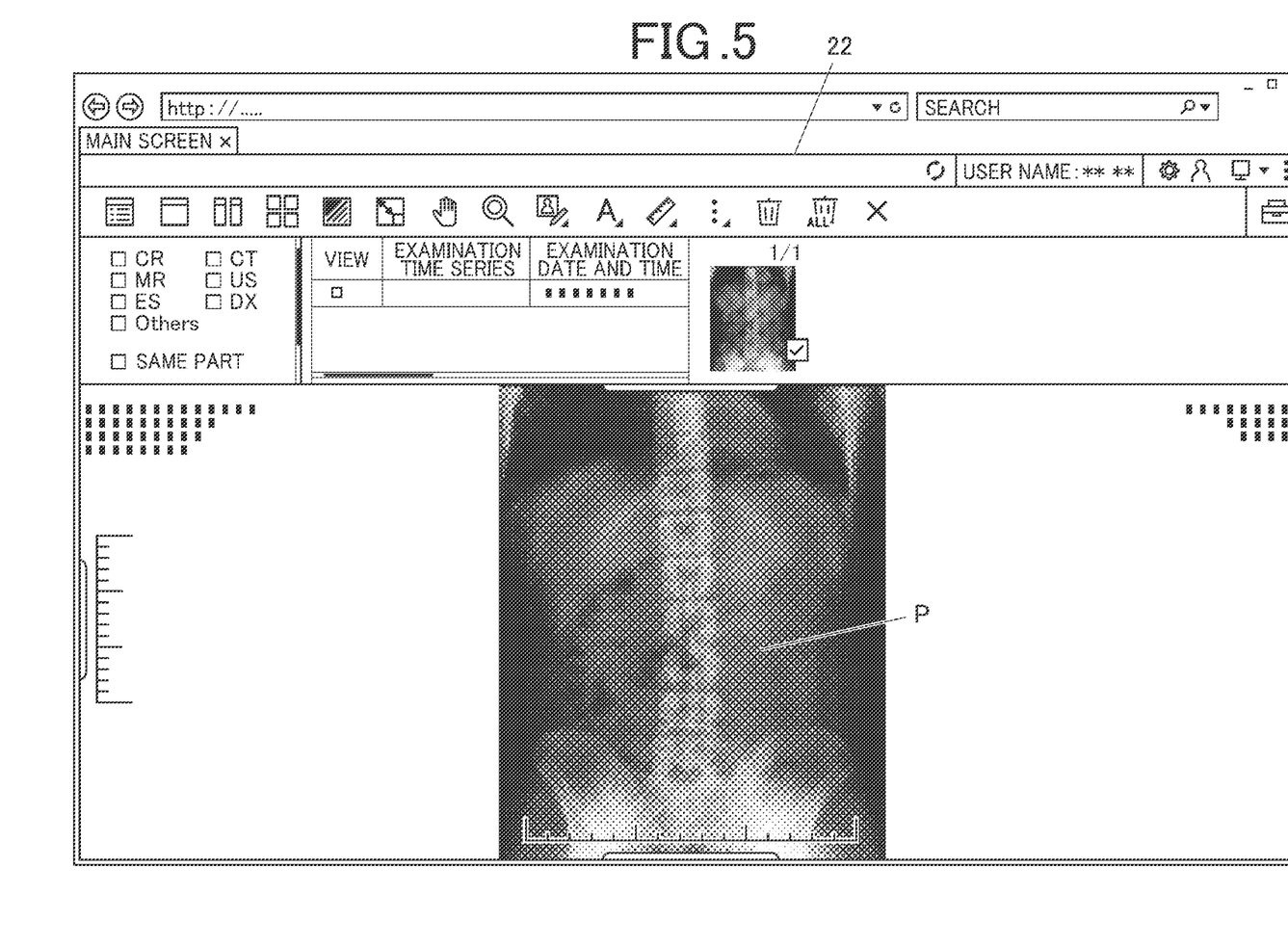
FIG. 5 is a schematic diagram of a main screen displaying medical image data as a medical image.

The controller 21 causes the display 22 to display a list screen as shown in FIG. 3 or a main screen having a display region for medical image data in the center as shown in FIG. 5, for example.

The controller 21 displays the medical image data in a viewing format as the medical image P in the display region (display 22) of the main screen.

In one or more embodiments, the main screen or the medical image P displayed thereon is web contents displayed by the browser that the medical image display terminal 20 originally has. Using a browser eliminates the need to explicitly install an application or the like on the medical image display terminal 20. In addition, even if the first medical image display terminal 20 fails or the battery runs out, it is possible to use the second medical image display terminal 20 connected to the network NW. In addition, maintenance such as updating the application of the medical image display terminal 20 according to the updating of the console program may be unnecessary, which is advantageous.

Various processing programs (or instructions) can also be transmitted to the medical image display terminal 20 as web contents. In this case, it is possible to use JavaScript (registered trademark) or WebAssembly format that can be executed on a web browser.

The list screen and the main screen are not limited to the forms shown in FIGS. 3 and 5. In particular, a configuration may be adopted in which only the medical image P selected on the list screen is displayed on the display 22 without providing the main screen.

The number of medical images P displayed on the main screen is not limited to one, and a plurality of medical images P may be displayed for the purpose of comparative interpretation.

[Operation of a Medical Image Display System]

Next, an operation of the medical image display system 100 will be described.

Figure 6:
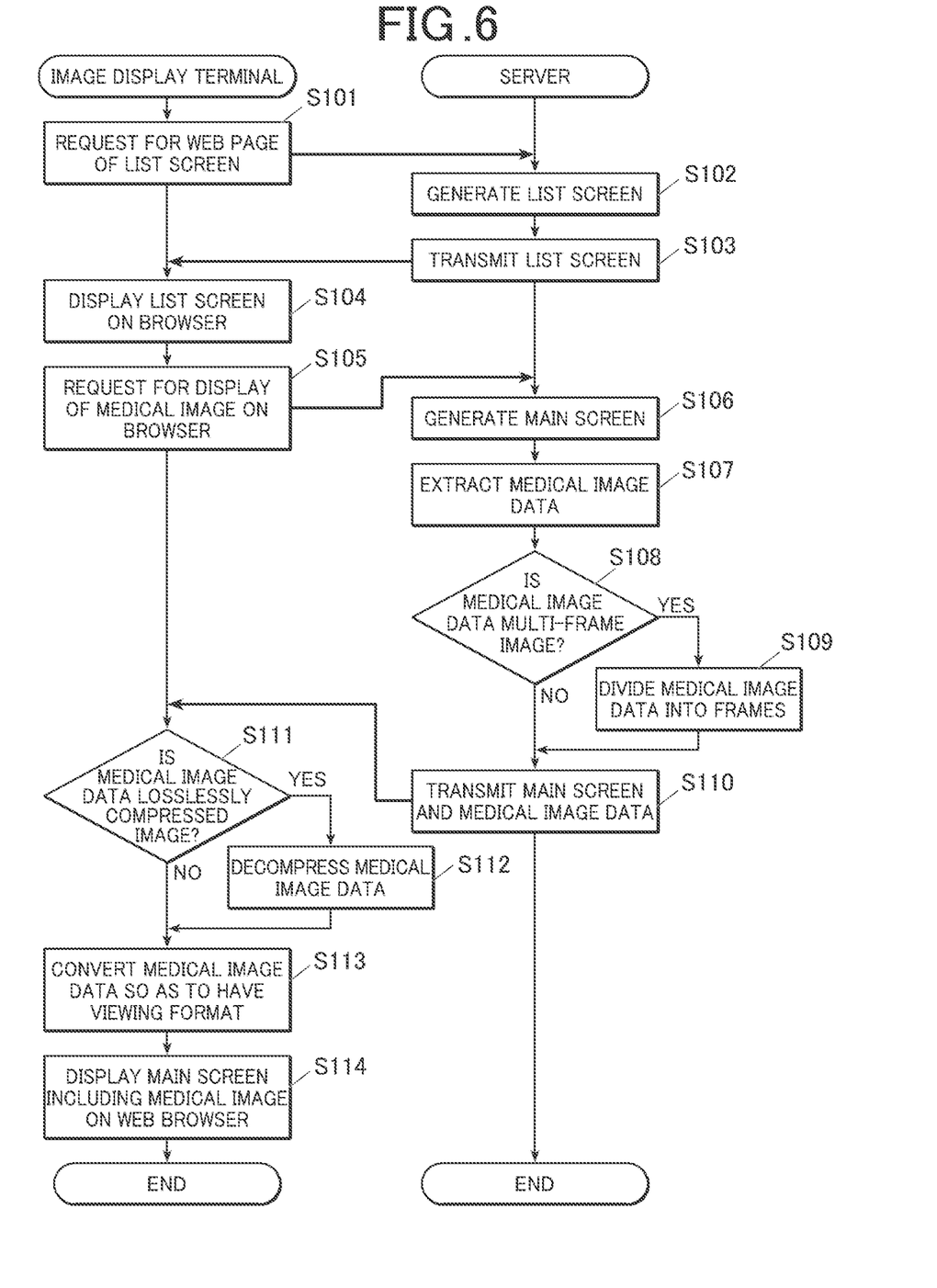
FIG. 6 is a ladder flowchart showing an image display flow according to one or more embodiments.

FIG. 6 is a ladder flowchart showing image display processing in the medical image display system 100 in which the medical image display terminal 20 converts medical image data in a storage format stored in the server 10 into medical image data in a viewing format and displays the medical image data in the viewing format as the medical image P on the web browser.

In one or more implementations, the ladder flowchart starts when a user using the medical image display terminal 20 inputs a specific URL represented by the IP information or the like of the server 10 to the web browser and receives login authentication.

First, when the user of the medical image display terminal 20 gives an instruction to display a list screen through the operation interface 23, the controller 21 transmits a signal requesting the web page of the list screen to the server 10 through the communicator 24 (step S101).

When the communicator 12 of the server 10 receives the signal from the medical image display terminal 20, the controller 11 generates the list screen based on the contents of the medical image data database stored in the storage 13 (step S102) and transmits the list screen to the medical image display terminal 20 through the communicator 12 (step S103).

When the communicator 24 of the medical image display terminal 20 receives the list screen, the controller 21 causes the display 22 to display the list screen (step S104).

Then, when the user of the medical image display terminal 20 gives an instruction to display the medical image P from the list screen through the operation interface 23, the controller 21 transmits a signal requesting the display of the medical image P to the server 10 through the communicator 24 (step S105).

When the communicator 12 of the server 10 receives a transmission request signal for medical image data from the medical image display terminal 20, the controller 11 generates a main screen (step S106). The controller 11 extracts the corresponding medical image data from the storage 13 (step S107) and determines whether the medical image data is a multi-frame image (step S108).

If the medical image data is not a multi-frame image (that is, if the medical image data is a single-frame image) (step S108; No), the main screen and the medical image data are transmitted to the medical image display terminal 20 by the communicator 12 (step S110).

If the medical image data is a multi-frame image (step S108; Yes), the controller 11 performs division processing to divide the multi-frame image into frames (step S109) and transmits the main screen and the divided medical image data frame by frame to the medical image display terminal 20 through the communicator 12 (step S110).

When the communicator 24 of the medical image display terminal 20 receives the medical image data from the server 10, the controller 21 determines whether the medical image data is a losslessly compressed image (step S111).

If the medical image data is not a losslessly compressed image (that is, if the medical image data is a lossy-compressed image) (step S111; No), the controller 21 converts the medical image data to a viewing format using a conversion processing program (step S113).

If the medical image data is a losslessly compressed image (step S111; Yes), the controller 21 performs decompression processing on the medical image data using the decompression processing program (step S112), and then converts the medical image data to a viewing format using the conversion processing program (step S113).

As the decompression processing program and the conversion processing program used in steps S112 and S113, those stored in the storage 13 may be transmitted through the communicator 12 together with the medical image data. Alternatively, the medical image display terminal 20 may acquire the decompression processing program and the conversion processing program used in steps S112 and S113 from another server. The decompression processing program and the conversion processing program used in steps S112 and S113 may be stored in advance in the storage 25 of the medical image display terminal 20, and implementations are not particularly limited to the above examples.

Then, the controller 21 causes the display 22 to display the main screen including the medical image P based on the medical image data converted to a viewing format in step S113 (step S114).

As described above, the medical image display system 100 according to one or more embodiments includes the server 10 and the medical image display terminal 20 capable of communicating with the server 10. The server 10 includes the storage 13 that stores medical image data in a storage format and the communicator 12 as a first transmitter that transmits the medical image data in the storage format to the medical image display terminal 20. The medical image display terminal 20 includes the controller 21 as a first conversion processor that converts the medical image data in the storage format transmitted from the server 10 into medical image data in a viewing format that can be viewed on the web browser and the display 22 that displays the medical image P based on the medical image data in the viewing format on the web browser.

According to this configuration, it is not necessary to store the medical image data in a viewing format in the server 10. Therefore, since the larger capacity of the storage 13 is not required, it is possible to suppress the cost for the storage 13. In addition, since the medical image data is converted from the storage format to the viewing format by the medical image display terminal 20 instead of the server 10, the burden on the server 10 is reduced.

When the medical image data is losslessly compressed, the controller 21 serving as the first conversion processor of the medical image display terminal 20 decompresses the losslessly compressed medical image data.

According to this configuration, the losslessly compressed image data can be stored in the storage 13 of the server 10. Therefore, since it is not necessary to increase the capacity of the server 10, it is possible to further suppress the cost. In addition, it is possible to suppress the amount of communication between the server 10 and the medical image display terminal 20.

The server 10 includes the controller 11 serving as a frame division processor that performs division processing to divide the medical image data into frames when the medical image data to be transmitted to the medical image display terminal 20 is a multi-frame image. The server 10 transmits the medical image data in a storage format divided into frames.

According to this configuration, even a multi-frame image with a large volume can be easily transmitted to the medical image display terminal 20. In addition, it is possible to suppress the amount of communication between the server 10 and the medical image display terminal 20.

In the above description, an example in which the server 10 generates the list screen and the main screen is provided. However, the present invention is not limited to this example, and the medical image display terminal 20 may generate the list screen and the main screen.

MODIFICATION EXAMPLES

In the above description, the server 10 always transmits the medical image data to the medical image display terminal 20, and the medical image display terminal 20 always converts the transmitted medical image data into a viewing format. However, when a predetermined condition is satisfied, the server 10 may convert the medical image data to a viewing format.

Figure 7:
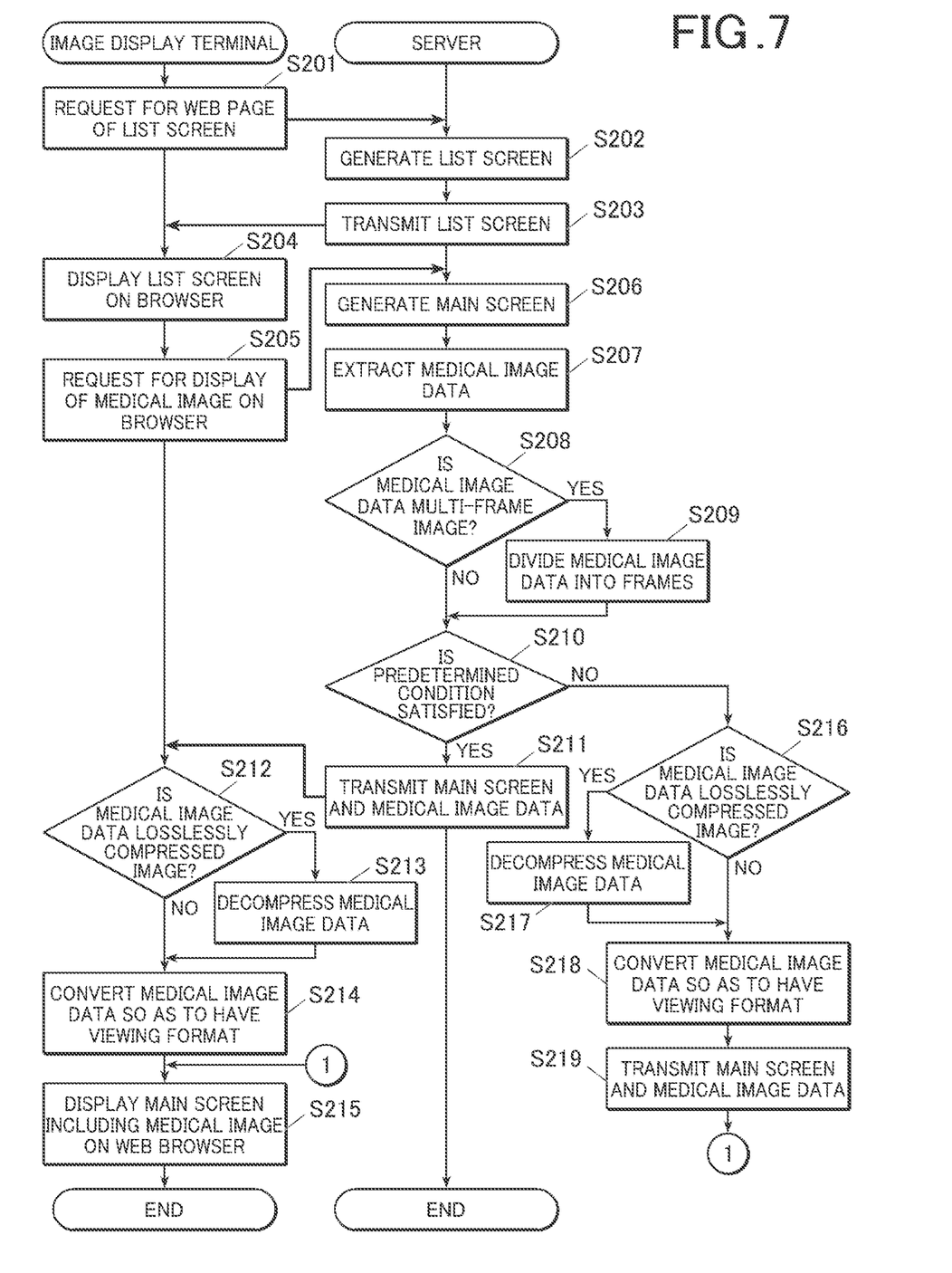
FIG. 7 is a ladder flowchart showing an image display flow according to a modification example.

Image display processing in this configuration will be described with reference to the ladder flowchart in FIG. 7.

Detailed descriptions of steps S201 to S209, which are the same as in the image display processing according to the above embodiments, will be omitted.

After extracting the medical image data designated by the medical image display terminal 20 and performing division processing to divide into frames if the medical image data is a multi-frame image in steps S207 to S209, the controller 11 determines whether a predetermined condition is satisfied (step S210). If the predetermined condition is satisfied (step S210; Yes), the controller 11 causes the medical image display terminal 20 to convert the medical image data to a viewing format (steps S212 to S215).

The "predetermined condition" in this modification example is whether the amount of medical image data is equal to or less than a predetermined value.

That is, only when the amount of the medical image data is equal to or less than the predetermined value (step S210; Yes), the medical image data in a storage format is transmitted to the medical image display terminal 20 to cause the controller 21 to perform format conversion as a first conversion processor (steps S211 to S215).

On the other hand, if the amount of the medical image data is equal to or greater than the predetermined value (step S210; No), the controller 11 determines that the server 10 converts the format of the medical image data. Then, it is determined whether the medical image data is a losslessly compressed image (step S216). If the medical image data is a losslessly compressed image (step S216; Yes), decompression processing is performed (step S217), and then the medical image data is converted to a viewing format (step S218). If the medical image data is a lossy-compressed image (step S216; No), the medical image data is converted to a viewing format (step S218).

After converting the medical image data to a viewing format, the controller 11 transmits the main screen and the medical image data to the medical image display terminal 20 through the communicator 12 (step S219), and causes the display 22 to display the main screen including the medical image P based on the medical image data (step S215).

As described above, in one or more embodiments, the controller 11 of the server 10 is used as a determinator, and only when the predetermined condition that the amount of medical image data is equal to or greater than a predetermined value is satisfied, the controller 21 is caused to convert the medical image data to a viewing format as the first conversion processor of the medical image display terminal 20. In other embodiments, the controller 11 is caused to convert the medical image data to a viewing format as the second conversion processor of the server 10.

Generally, the server 10 is superior in processing capacity to the medical image display terminal 20. When the amount of medical image data requested for display is too large (for example, when the medical image data is mammography), the overall processing speed may be slowed down if the controller 21 of the medical image display terminal 20 is caused to convert the medical image data to a viewing format. However, by determining which of the server 10 and the medical image display terminal 20 should convert the medical image data to a viewing format according to the amount of medical image data as in this modification example, it is possible to increase the overall processing speed.

The predetermined condition is not limited to the amount of medical image data, and may be the processing capacity of the medical image display terminal 20, for example.

That is, before transmitting the medical image data in the storage format, a processing capacity measurement program may be transmitted to the medical image display terminal 20 to measure the processing capacity of the medical image display terminal 20. When it is determined in step S210 that the medical image display terminal 20 does not have enough CPU or memory to convert the medical image data to a viewing format, the controller 11 of the server 10 may perform format conversion.

For example, the communication speed estimated from the communication standard between the server 10 and the medical image display terminal 20 may be used as the predetermined condition.

Specifically, in the case of wired LAN connection, determination is made according to whether the link speed is 100 Mbps or 1000 Gbps. In the case of wireless LAN connection, determination is made according to whether the maximum communication speed is defined by the communication standard such as 802.11a/b/g/n/ac.

The predetermined condition is not limited to one condition, and a plurality of conditions may be set. In such instances, if even one of a plurality of predetermined conditions is satisfied, it may be determined that format conversion is to be performed on any side, or the determination may be made after giving a weighting to each of the plurality of predetermined conditions.

If the server 10 is controlled to preferentially convert the medical image data to a viewing format and the server 10 does not have enough CPU or memory to convert the medical image data to a viewing format, determination may be made such that the medical image display terminal 20 performs format conversion. Alternatively, by estimating and comparing the processing speed when the format conversion is performed by the server 10 and the processing speed when the format conversion is performed by the medical image display terminal 20, it may be determined that the format conversion is performed by the faster one.

[Other Configurations]

When an image is displayed on the medical image display terminal 20, if secondary capture is performed by image editing or the like by the controller 21 as a first image editor, only the image editing information may be transmitted to the server 10 and the medical image data may be edited by the controller 11 as a second image editor based on the image editing information.

With such a configuration, the amount of communication between the server 10 and the medical image display terminal 20 can be suppressed more than transmitting the secondary capture to the server 10.

When various processing programs (or instructions) are transmitted from the server 10 to the medical image display terminal 20, processing for caching the processing program once acquired in the browser or processing for reacquiring the processing program only when the version is different may be included for the corresponding processing program. This speeds up the processing because it is not necessary to transmit and receive the processing program more than necessary at the time of second and subsequent image displays.

The processing program may include processing for deleting the medical image data or parameters stored in the storage 25 based on an operation such as closing the browser. In this manner, the patient's personal information does not remain in the medical image display terminal 20 after the end of image display, which serves the data security.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A medical image display system, comprising:
a server; and
a medical image display terminal that communicates with the server, wherein
the server comprises:
a storage that stores medical image data in a storage format;
a server hardware processor that:
determines whether to cause the medical image display terminal to convert the medical image data in the storage format into the medical image data in a viewing format that is viewable on a web browser based on a predetermined condition, and
upon determining not to cause the medical image display terminal to convert the medical image data in the storage format into the medical image data in the viewing format, converts the medical image data in the storage format into the medical image data in the viewing format; and
a server transmitter that transmits the medical image data in the storage format to the medical image display terminal, and
the medical image display terminal comprises:
a terminal hardware processor that converts the medical image data in the storage format transmitted from the server into the medical image data in the viewing format in a case where the server hardware processor determines to cause the medical image display terminal to convert the medical image data in the storage format into the medical image data in the viewing format; and
a display that displays a medical image based on the medical image data in the viewing format on the web browser.

2. The medical image display system according to claim 1, wherein
the storage stores instructions to convert the medical image data in the storage format into the medical image data in the viewing format,
the server transmitter transmits the instructions to the medical image display terminal, and
the terminal hardware processor converts the medical image data in the storage format into the medical image data in the viewing format by using the instructions.

3. The medical image display system according to claim 1,
wherein the medical image data in the storage format has a DICOM format.

4. The medical image display system according to claim 1, wherein
in a case that the medical image data in the storage format is losslessly compressed, the terminal hardware processor decompresses the losslessly compressed medical image data.

5. The medical image display system according to claim 1, wherein
the server hardware processor divides the medical image data into frames in a case that the medical image data in the storage format to be transmitted to the medical image display terminal is a multi-frame image, and
the server transmitter transmits the medical image data in the storage format divided into the frames.

6. The medical image display system according to claim 1, wherein
the predetermined condition is defined based on an amount of the medical image data, and
in a case that the amount of the medical image data is equal to or greater than a predetermined value, the server hardware processor determines not to cause the medical image display terminal to convert the medical image data in the storage format into the medical image data in the viewing format.

7. The medical image display system according to claim 1, wherein
the predetermined condition is defined based on a processing capacity of the medical image display terminal, and
in a case that the processing capacity of the medical image display terminal is equal to or less than a predetermined value, the server hardware processor determines not to cause the medical image display terminal to convert the medical image data in the storage format into the medical image data in the viewing format.

8. The medical image display system according to claim 1, wherein
the terminal hardware processor edits the medical image data in the viewing format,
the medical image display terminal further comprises:
a terminal transmitter that transmits editing information to the server, and
the server hardware processor edits the medical image data in the storage format based on the editing information.

* * * * *